United States Patent
Komuro

(10) Patent No.: US 9,579,156 B2
(45) Date of Patent: Feb. 28, 2017

(54) SURGICAL OPERATION SUPPORT SYSTEM AND SURGICAL INSTRUMENT

(71) Applicant: OLYMPUS CORPORATION, Tokyo (JP)

(72) Inventor: Takahiro Komuro, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 736 days.

(21) Appl. No.: 13/967,432

(22) Filed: Aug. 15, 2013

(65) Prior Publication Data
US 2013/0331860 A1 Dec. 12, 2013

Related U.S. Application Data

(63) Continuation of application No. PCT/JP2012/057669, filed on Mar. 16, 2012.

(30) Foreign Application Priority Data

Mar. 17, 2011 (JP) ................. 2011-059850

(51) Int. Cl.
*A61B 19/00* (2006.01)
*A61B 17/00* (2006.01)

(52) U.S. Cl.
CPC .......... *A61B 19/2203* (2013.01); *A61B 34/30* (2016.02); *A61B 34/70* (2016.02);
(Continued)

(58) Field of Classification Search
CPC ..... A61B 34/30; A61B 19/2203; A61B 34/70; A61B 2090/0803; B65D 2583/0409; A61J 7/0084
See application file for complete search history.

(56) References Cited

U.S. PATENT DOCUMENTS 2,416,081 A * 2/1947 Bakke ................. G06M 1/143
188/158
5,508,836 A * 4/1996 DeCaro ................ H04B 10/11
398/1

(Continued)

FOREIGN PATENT DOCUMENTS

JP 2-64962 5/1990
JP 09-197541 A 7/1997
(Continued)

OTHER PUBLICATIONS

International Search Report dated Apr. 17, 2012 issued in PCT/JP2012/057669.

(Continued)

*Primary Examiner* — Ashley Fishback
(74) *Attorney, Agent, or Firm* — Scully, Scott, Murphy & Presser, P.C.

(57) ABSTRACT

A surgical operation support system includes: a surgical instrument provided with a usage count accumulation portion that includes a moving portion and a moving mechanism which is configured to move the moving portion; and a body which includes a driving portion that is configured to move the moving portion through the moving mechanism. The usage count accumulation portion is configured to accumulate a usage count of the surgical instrument by a movement of the moving portion.

11 Claims, 10 Drawing Sheets

(52) U.S. Cl.
CPC ............... *A61B 2017/00477* (2013.01); *A61B 2090/0803* (2016.02)

(56) References Cited

U.S. PATENT DOCUMENTS

| | | | |
|---|---|---|---|
| 6,331,181 B1 | 12/2001 | Tierney et al. | |
| 6,601,748 B1 | 8/2003 | Fung et al. | |
| 7,124,932 B2 * | 10/2006 | Isaacson ................ | A61B 18/12 235/144 SM |
| 2007/0156285 A1 | 7/2007 | Sillman et al. | |
| 2007/0175960 A1 | 8/2007 | Shelton, IV et al. | |
| 2008/0029572 A1 | 2/2008 | Shelton et al. | |
| 2009/0139516 A1 | 6/2009 | Augustyn et al. | |

FOREIGN PATENT DOCUMENTS

| | | |
|---|---|---|
| JP | 2001-000386 A | 1/2001 |
| JP | 2003-052717 A | 2/2003 |
| JP | 2005-237586 A | 9/2005 |
| JP | 2007-222615 A | 9/2007 |
| JP | 2007-526562 A | 9/2007 |
| JP | 2010-220955 A | 10/2010 |
| JP | 2010-268844 A | 12/2010 |
| JP | 2011-194129 A | 10/2011 |
| WO | 2005/079727 A2 | 9/2005 |

OTHER PUBLICATIONS

Extended Supplementary European Search Report dated Nov. 19, 2014 from related European Application No. 12 75 8073.6.

\* cited by examiner ically installed and which includes a driving portion
SURGICAL OPERATION SUPPORT SYSTEM AND SURGICAL INSTRUMENT This application is a continuation application based on a PCT Patent Application No. PCT/JP2012/057669, filed Mar. 16, 2012, whose priority is claimed on Japanese Patent Application No. 2011-059850, filed Mar. 17, 2011. The contents of both the PCT Patent Application and the Japanese Patent Application are incorporated herein by reference.

BACKGROUND OF THE INVENTION

Field of the Invention

The present invention relates to a surgical operation support system on which a surgical instrument is mounted for use, and to a surgical instrument which is used for the surgical operation support system.

Description of Related Art

In recent years, in order to reduce invasiveness in surgical operations, robots have been introduced for studying medical treatment and in clinical field. Particularly, in the field of surgery, various medical manipulator systems (surgical operation support systems) which treat a patient by a multi-degrees-of-freedom manipulator including a multi-degrees-of-freedom arm have been suggested. In this medical manipulator system, various surgical instruments such as a gripper (a gripping portion) and forceps, or the like are mounted on the tip of the arm. These surgical instruments have been disposed. However, in recent years, by performing treatment such as sterilization, or the like, it has been possible to use the same surgical instruments more than once by mounting on the tip of the arm. However, these surgical instruments are members deteriorating as they are used more than once, and there is a possibility that the deterioration will cause problems in using the instruments. In order to prevent the problems, it is necessary to use the surgical instrument with the accurate ascertainment of the use limit (life) of the surgical instrument mounted on the tip of the arm.

U.S. Pat. No. 6,331,181 discloses a configuration in which the usage count or the like of a surgical instrument can be recorded by mounting a memory on the surgical instrument. In this configuration, when the surgical instrument is mounted on the arm, the usage count of the surgical instrument that is recorded in the memory can be read.

SUMMARY OF THE INVENTION

According to a first aspect of the present invention, a surgical operation support system includes: a surgical instrument provided with a usage count accumulation portion that includes a moving portion which is movably configured and a moving mechanism which is configured to move the moving portion; and a body in which the surgical instrument is detachably installed and which includes a driving portion that is configured to move the moving portion by a predetermined amount through the moving mechanism when the surgical instrument is attached to or detached from the body. The usage count accumulation portion is configured to accumulate a usage count of the surgical instrument by a movement of the moving portion.

According to a second aspect of the present invention, in the surgical operation support system according to the first aspect, the driving portion may be configured to move the moving portion by the predetermined amount while contacting the moving portion when the surgical instrument is attached to or detached from the body.

According to a third aspect of the present invention, in the surgical operation support system according to the second aspect, the moving portion may be a gear that is configured to move while rotating. The moving mechanism may be configured to rotate the gear by moving. The driving portion may be a columnar portion that is configured to move the moving mechanism when the surgical instrument is attached to or detached from the body.

According to a fourth aspect of the present invention, in the surgical operation support system according to the second aspect, the moving portion may be a first gear that is configured to move while rotating. The moving mechanism may include a second gear that is configured to rotate via a link mechanism, and may be configured to rotate the first gear by rotation of the second gear. The driving portion may be a columnar portion that is configured to operate the link mechanism when the surgical instrument is attached to or detached from the body.

According to a fifth aspect of the present invention, in the surgical operation support system according to the second aspect, the moving portion may be a linear driving member that is provided with concave portions at a constant interval and is configured to move in a linear direction. The moving mechanism may be configured to move the linear driving member by moving a member that is configured to move in a direction orthogonal to the linear direction, and may be configured to restrict the linear driving member to move in a constant direction by a restriction member. The driving portion may be a columnar portion that is configured to operate the moving mechanism when the surgical instrument is attached to or detached from the body.

According to a sixth aspect of the present invention, in the surgical operation support system according to the first aspect, the driving portion may be configured to move the moving portion by the predetermined amount without contacting the moving portion when the surgical instrument is attached to or detached from the body.

According to a seventh aspect of the present invention, in the surgical operation support system according to the sixth aspect, the moving portion may be a gear that is configured to move while rotating. The moving mechanism may have a first magnet, and may be configured to rotate the gear by moving due to magnetic force applied to the first magnet. The driving portion may include a second magnet that is configured to apply the magnetic force to the first magnet when the surgical instrument is attached to or detached from the body.

According to an eighth aspect of the present invention, in the surgical operation support system according to any one of the first aspect to the seventh aspect, the usage count accumulation portion may include a potentiometer that is configured to change a resistance value according to a movement amount of the moving portion. The surgical instrument may further include an output portion that is configured to output the resistance value of the potentiometer to the body as a voltage value.

According to a ninth aspect of the present invention, in the surgical operation support system according to the eighth aspect, the output portion may include electrodes that are connected to the potentiometer and are configured to output the resistance value of the potentiometer to the body as the voltage value by being electrically connected to the driving portion when the surgical instrument is mounted on the body.

According to a tenth aspect of the present invention, in the surgical operation support system according to the eighth aspect, the output portion may include a wireless communication portion that is connected to the potentiometer and is configured to wirelessly communicate the resistance value of the potentiometer to the body as the voltage value.

According to an eleventh aspect of the present invention, in the surgical operation support system according to the third aspect, each tooth of the gear may be formed such that the each tooth has a different height from a center of the gear. The body may further include a sensor that is configured to read the height of the each tooth when the body is mounted on the surgical instrument, and a rotation angle detection portion that is configured to detect a rotation angle of the gear based on the height of the each tooth read by the sensor.

According to a twelfth aspect of the present invention, in the surgical operation support system according to the fourth aspect, each tooth of the first gear may be formed such that the each tooth has a different height from a center of the first gear. The body may further include a sensor that is configured to read the height of the each tooth when the body is mounted on the surgical instrument, and a rotation angle detection portion that is configured to detect a rotation angle of the first gear based on the height of the each tooth read by the sensor.

According to a thirteenth aspect of the present invention, in the surgical operation support system according to any one of the first aspect to the twelfth aspect, the surgical instrument may further include a usage count restriction portion that is configured to restrict the usage count of the surgical instrument by restricting a movement amount of the moving portion.

According to a fourteenth aspect of the present invention, in the surgical operation support system according to any one of the first aspect to the thirteenth aspect, numbers configured to indicate the usage count of the surgical instrument may be formed in the moving portion. An opening portion configured to read the numbers formed in the moving portion from an outside may be formed in the surgical instrument.

According to a fifteenth aspect of the present invention, a surgical instrument, which is freely attached to or detached from a body of a surgical operation support system, includes a usage count accumulation portion that includes a moving portion which is movably configured and a moving mechanism which is configured to move the moving portion when the surgical instrument is attached to or detached from the body. The usage count accumulation portion is configured to accumulate a usage count of the surgical instrument by a movement of the moving portion.

According to a sixteenth aspect of the present invention, in the surgical instrument according to the fifteenth aspect, the moving portion may be a gear that is configured to move while rotating. The moving mechanism may be configured to rotate the gear when the surgical instrument is attached to or detached from the body.

According to a seventeenth aspect of the present invention, in the surgical instrument according to the fifteenth aspect, the moving portion may be a first gear that is configured to move while rotating. The moving mechanism may include a second gear that is configured to rotate via a link mechanism when the surgical instrument is attached to or detached from the body, and may be configured to rotate the first gear by rotation of the second gear.

According to an eighteenth aspect of the present invention, in the surgical instrument according to the fifteenth aspect, the moving portion may be a linear driving member that is provided with concave portions at a constant interval and is configured to move in a linear direction. The moving mechanism may be configured to move the linear driving member by moving a member that is configured to move in a direction orthogonal to the linear direction when the surgical instrument is attached to or detached from the body, and may be configured to restrict the linear driving member to move in a constant direction by a restriction member.

According to a nineteenth aspect of the present invention, in the surgical instrument according to the fifteenth aspect, the moving portion may be a gear that is configured to move while rotating. The moving mechanism may include a first magnet, and may be configured to rotate the gear by moving due to magnetic force applied by the first magnet when the surgical instrument is attached to or detached from the body.

According to a twentieth aspect of the present invention, the surgical instrument according to any one of the fifteenth aspect to the nineteenth aspect may further include an output portion that is configured to output a resistance value of a potentiometer to the body as a voltage value. The usage count accumulation portion may include the potentiometer that is configured to change the resistance value according to a movement amount of the moving portion.

According to a twenty-first aspect of the present invention, in the surgical instrument according to the twentieth aspect, the output portion may include electrodes that are connected to the potentiometer and are configured to output the resistance value of the potentiometer to the body as the voltage value by being electrically connected to the body when the surgical instrument is mounted on the body.

According to a twenty-second aspect of the present invention, in the surgical instrument according to the twentieth aspect, the output portion may include a wireless communication portion that is connected to the potentiometer and is configured to wirelessly communicate the resistance value of the potentiometer to the body as the voltage value.

According to a twenty-third aspect of the present invention, in the surgical instrument according to the sixteenth aspect, each tooth of the gear may be formed such that the each tooth has a different height from a center of the gear, and may be configured such that the height of the each tooth is read when the surgical instrument is mounted on the body.

According to a twenty-fourth aspect of the present invention, in the surgical instrument according to the seventeenth aspect, each tooth of the first gear may be formed such that the each tooth has a different height from a center of the first gear, and may be configured such that the height of the each tooth is read when the surgical instrument is mounted on the body.

According to a twenty-fifth aspect of the present invention, the surgical instrument according to any one of the fifteenth aspect to the twenty-fourth aspect may further include a usage count restriction portion that is configured to restrict the usage count of the surgical instrument by restricting a movement amount of the moving portion.

According to a twenty-sixth aspect of the present invention, in the surgical instrument according to any one of the fifteenth aspect to the twenty-fifth aspect, numbers for indicating the usage count of the surgical instrument may be formed in the moving portion. An opening portion configured to read the numbers formed in the moving portion from an outside may be formed in the surgical instrument.

BRIEF DESCRIPTION OF THE INVENTION

DETAILED DESCRIPTION OF THE INVENTION

Hereinafter, embodiments of the present invention are described with reference to drawings.

First Embodiment

Figure 1A:
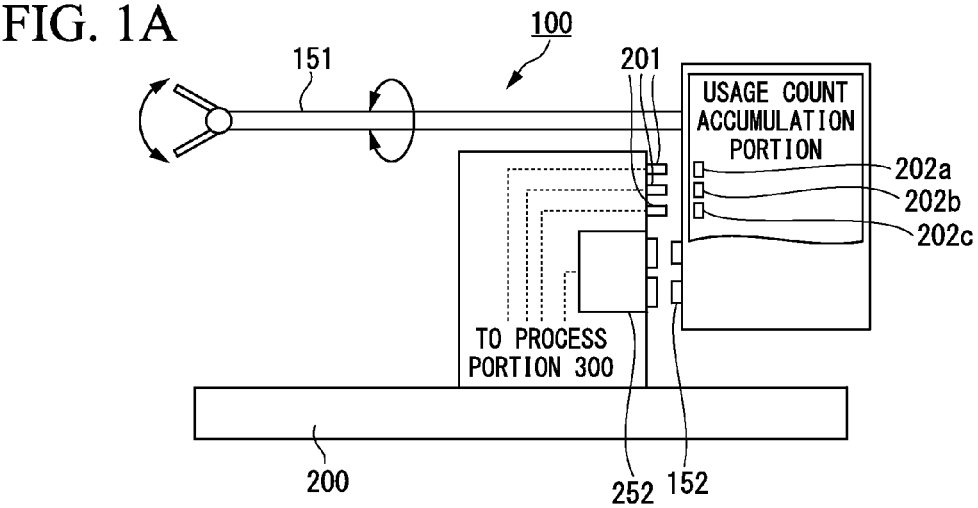
FIG. 1A is a view showing a configuration of a surgical operation support system according to a first embodiment of the present invention.
Figure 1B:
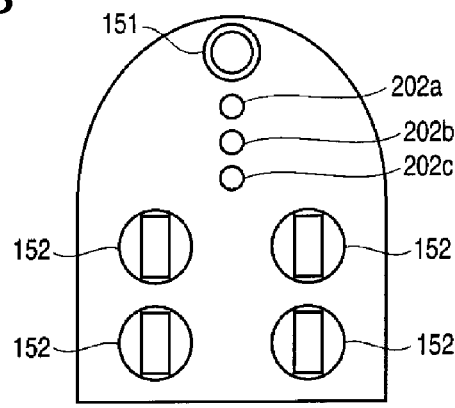
FIG. 1B is a view showing the configuration of the surgical operation support system according to the first embodiment of the present invention.
Figure 1C:
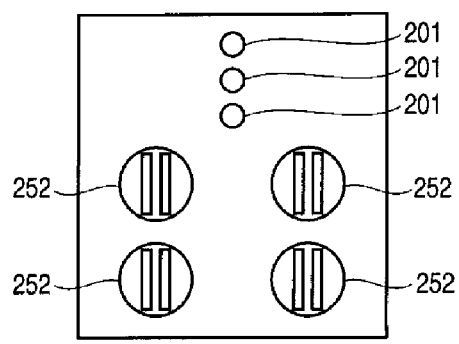
FIG. 1C is a view showing the configuration of the surgical operation support system according to the first embodiment of the present invention.

First, a first embodiment of the present invention is described. FIGS. 1A to 1C are views showing a configuration of a surgical operation support system according to the first embodiment of the present invention. FIG. 1A is a lateral view of the surgical operation support system according to the present embodiment. FIG. 1B shows a portion of a surgical instrument that is attached to or detached from an arm portion. FIG. 1C shows a portion of the arm which the surgical instrument is attached to or detached from.

As shown in FIG. 1A, the surgical operation support system according to the present embodiment includes a surgical instrument 100 and an arm portion (a body) 200. The surgical instrument 100 is configured to be freely attached to or detached from the arm portion 200. A movable portion 151 is provided at a distal end of the surgical instrument 100. This movable portion 151 is connected to a torque transmission portion 152 and operates in conjunction with the operation of the torque transmission portion 152. In the present embodiment, the configuration of the movable portion 151 is not limited. FIGS. 1A to 1C show an example in which as the movable portion 151 that operates in conjunction with the operation of the torque transmission portion 152, a gripping device (gripper), which rotates, bends, and is closed or opened, is provided. The movable portion 151 may be a treatment tool such as a needle-holder, scissors, or an electrosurgical knife.

Figure 2:
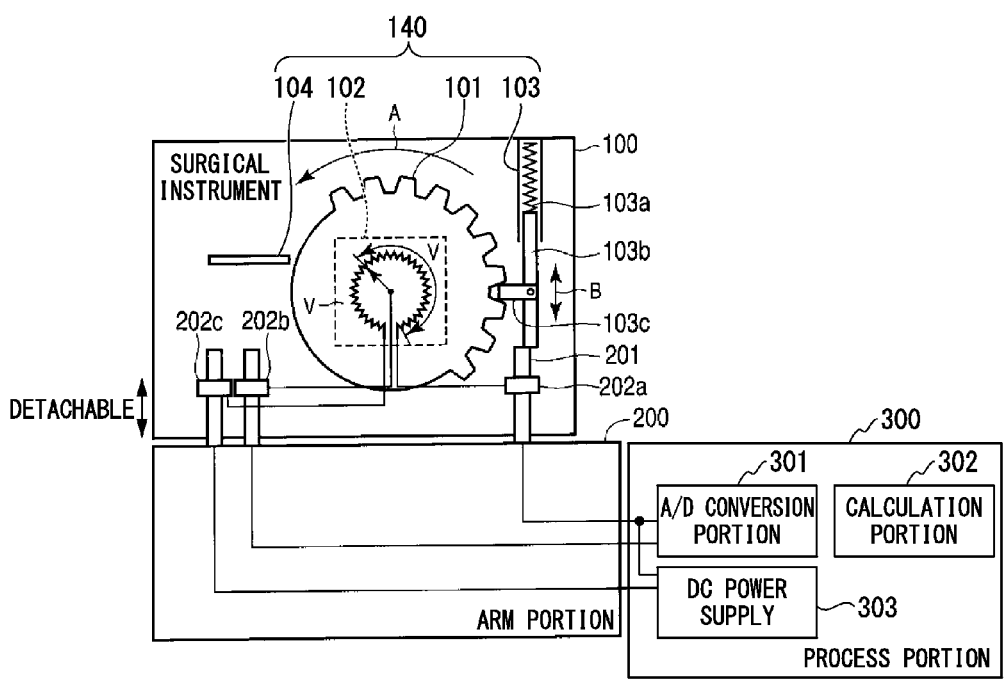
FIG. 2 is a view showing the detail of a usage count accumulation portion of a surgical instrument and an arm portion.

FIG. 2 is a view showing the detail of a usage count accumulation portion of the surgical instrument and the arm portion. FIG. 2 also shows a process portion 300 connected to the arm portion 200. The surgical instrument 100 includes the usage count accumulation portion 140. In FIG. 2, the usage count accumulation portion 140 includes a gear (a moving portion) 101, a potentiometer 102, a gear-moving mechanism (a moving mechanism) 103, and a rotation preventing member (a usage count restriction member) 104, as an example.

The gear 101 as a moving portion includes teeth with numbers corresponding at least to a limit value of the usage count of the surgical instrument 100. The gear 101 is rotatably supported on the body of the surgical instrument 100. FIG. 2 is an example in which the limit value of the usage count of the surgical instrument 100 is set to 10 times. In this case, at least 10 teeth are formed in the gear 101.

The potentiometer 102 is formed on the gear 101, and includes a rotating contact portion and a resistive element portion. The rotating contact portion is a metallic member that is configured to rotate in conjunction with the rotation of the gear. The rotating contact portion has an electrode that is electrically connected to an electrode 202a provided at the arm portion 200 when the surgical instrument 100 is mounted on the arm portion 200. The resistive element portion is a resistive element that is configured to contact the rotating contact portion. The resistive element portion has electrodes that are electrically connected to electrodes 202b and 202c provided at the arm portion 200 when the surgical instrument 100 is mounted on the arm portion 200. The potentiometer 102 having the above configuration changes a resistance value according to the rotation of the gear 101. The resistance value of the potentiometer 102 is detected as a voltage value V between the electrodes 202a and 202b.

Figure 3:
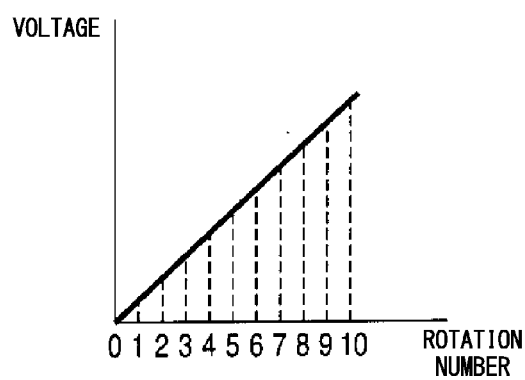
FIG. 3 is a view showing an example of a relationship between rotation number of a gear and a voltage value measured by a potentiometer.

The gear-moving mechanism 103 as a moving mechanism is a mechanism for rotating the gear 101. The gear-moving mechanism 103 is configured to rotate the gear 101 by a predetermined angle whenever the surgical instrument 100 is mounted on the arm portion 200. Accordingly, as shown in FIG. 3, a linear relationship is established between the rotation angle (corresponding to rotation number) of the gear 101 and the resistance value (detected as a voltage value V) of the potentiometer 102. Consequently, in the present embodiment, the rotation number of the gear 101 of the potentiometer 102, that is, the usage count of the surgical instrument 100 can be detected from the resistance value of the potentiometer 102.

The gear-moving mechanism 103 is described in more detail with reference to FIG. 2 and FIGS. 4A to 4C. As shown in FIG. 2, the gear-moving mechanism 103 has a coil spring 103a, a columnar portion 103b, and a movable portion 103c.

The coil spring 103a is configured such that when the surgical instrument 100 is mounted on the arm portion 200, the coil spring 103a is compressed by receiving a pressing force from the columnar portion 103b, and when the surgical instrument 100 is detached from the arm portion 200, the coil spring 103a returns to the original position.

Figure 4A:
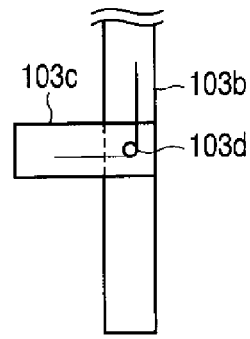
FIG. 4A is a view for illustrating the detail of a gear-moving mechanism according to the first embodiment of the present invention.

The columnar portion 103b is attached to the coil spring 103a such that the columnar portion 103b can move in the B direction shown in FIG. 2. The movable portion 103c is attached to the columnar portion 103b. As shown in FIG. 4A, the movable portion 103c is biased by a helical spring 103d so as to be at a right angle to the columnar portion 103b. Due to this configuration, the movable portion 103c is usually engaged with the gear 101 as shown in FIG. 2.

Figure 4B:
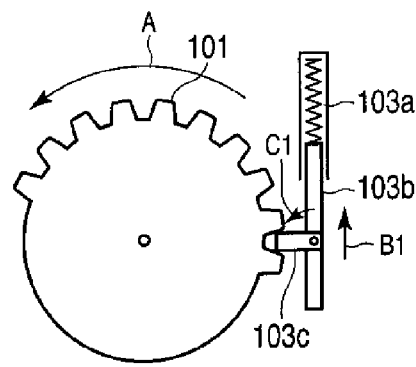
FIG. 4B is a view for illustrating the detail of the gear-moving mechanism according to the first embodiment of the present invention.

In the configuration shown in FIG. 4A, when the surgical instrument 100 is mounted on the arm portion 200, the columnar portion 103b of the surgical instrument 100 receives a pressing force in the B1 direction shown in FIG. 4B due to a columnar portion (a driving portion) 201 of the arm portion 200. Due to the pressing force in the B1 direction, the movable portion 103c abuts on the tooth of the gear 101 while being at a right angle to the columnar portion 103b, and a torque in the A direction shown in FIG. 4B is applied to the gear 101. Consequently, the gear 101 rotates by a predetermined angle according to the torque in the A direction applied by the movable portion 103c.

Figure 4C:
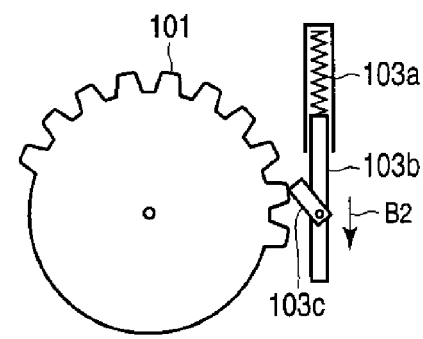
FIG. 4C is a view for illustrating the detail of the gear-moving mechanism according to the first embodiment of the present invention.

When the surgical instrument 100 is detached from the arm portion 200, the columnar portion 103b receives a pressing force in the B2 direction shown in FIG. 4C due to the restoring force of the coil spring 103a. Due to the pressing force in the B2 direction, the columnar portion 103b moves in the B2 direction. At this time, the movable portion 103c abuts on the tooth of the gear. However, by the action of the helical spring 103d, the movable portion 103c rotates, whereby the movable portion 103c is temporarily disengaged from the gear 101. Consequently, the gear 101 does not reversely rotate. Subsequently, due to the restoring force of the helical spring 103d, the movable portion 103c rotates in the C1 direction shown in FIG. 4B, whereby the movable portion 103c is engaged again with the gear 101.

Due to the configuration described above, it is possible to configure the gear-moving mechanism 103 that rotates the gear 101 in the A direction by a predetermined amount only when the surgical instrument 100 is mounted on the arm portion 200.

Herein, FIG. 2 is described again. The rotation preventing member 104 as a usage count restriction member is a member for restricting the rotation amount of the gear 101 in the A direction to a predetermined amount. This predetermined amount corresponds to a limit value of the usage count of the surgical instrument 100. For example, when the usage count of the surgical instrument 100 is restricted to 10 times, the position of the rotation preventing member 104 is determined such that the tooth of the gear 101 abuts on the rotation preventing member 104 after the gear 101 rotates by the amount corresponding to the 10 times so as to restrict the gear 101 from rotating any more.

The arm portion 200 as the body of the surgical operation support system has a power generation portion 252. The power generation portion 252 includes, for example, a motor and a power transmission mechanism, and is configured to be connected to the torque transmission portion 152 of the surgical instrument 100 when the surgical instrument 100 is mounted on the arm portion 200. The power generation portion 252 generates power for driving the movable portion 151 of the surgical instrument 100 by receiving control signals from a control portion (not shown) provided in the process portion 300, and transmits the power to the torque transmission portion 152. FIG. 1A shows an example of a configuration in which the movable portion 151 of the surgical instrument 100 is opened or closed by the torque transmission portion 152. However, the torque transmission portion 152 may carry out another operation such as moving the surgical instrument 100 from front to back and left to right.

The arm portion 200 has the columnar portion 201 and the electrodes 202a, 202b, and 202c.

The columnar portion 201 as driving portions are formed in the electrode 202a so as to have such a length that the columnar portion 201 applies a pressing force in the B1 direction shown in FIG. 4B to the columnar portion 103b by contacting the columnar portion 103b when the surgical instrument 100 is mounted on the arm portion 200.

The columnar portion 201 is an electric conductor. In addition, the electrodes 202a, 202b, and 202c are formed in a ring shape and connected to the potentiometer 102. When the surgical instrument 100 is mounted on the arm portion 200, the columnar portions 201 abut on the electrodes 202a, 202b, and 202c by being inserted in the ring of the electrodes 202a, 202b, and 202c, respectively, whereby the columnar portions 201 are connected to the potentiometer 102. The electrodes 202a and 202b are connected to an analogue/digital (A/D) conversion portion 301 of the process portion 300. In addition, the electrodes 202b and 202c are connected to a DC power supply 303.

The process portion 300 includes the A/D conversion portion 301, a calculation portion 302, and the DC power supply 303.

The DC power supply 303 functions to apply voltage to the potentiometer 102. In addition, the A/D conversion portion 301 converts the resistance value (the voltage value V) detected in the potentiometer 102 into a digital value. In accordance with the digital value converted in the A/D conversion portion 301, the calculation portion 302 accumulates a mounting count of the surgical instrument 100 as the usage count of the surgical instrument 100. The usage count of the surgical instrument 100 measured in the calculation portion 302 can be displayed on, for example, a predetermined display portion. A configuration can also be made such that when it is found that the usage count of the surgical instrument 100 reaches a limit value from the measurement result of the usage count of the surgical instrument 100, warning is provided.

As described above, according to the present embodiment, the usage count of the surgical instrument 100 can be mechanically measured. Accordingly, it is possible to configure a surgical instrument that is resistant to sterilization treatment or the like and is excellent in durability.

Figure 5A:
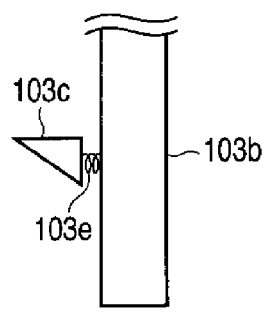
FIG. 5A is a view for illustrating a modified example of the gear-moving mechanism according to the first embodiment of the present invention.
Figure 5B:
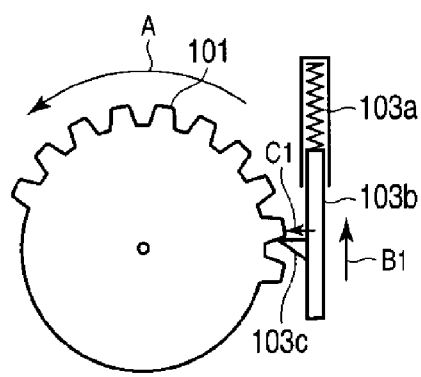
FIG. 5B is a view for illustrating a modified example of the gear-moving mechanism according to the first embodiment of the present invention.
Figure 5C:
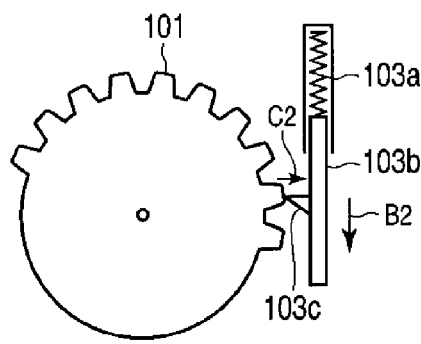
FIG. 5C is a view for illustrating a modified example of the gear-moving mechanism according to the first embodiment of the present invention.

The configuration of the gear-moving mechanism 103 is not limited to the configuration shown in FIGS. 4A to 4C. For example, the gear-moving mechanism 103 configured as shown in FIGS. 5A to 5C may also be used. In FIG. 4A, the movable portion 103c is attached to the columnar portion 103b by the helical spring 103d. However, in this modified example, the movable portion 103c is attached to the columnar portion 103b by a coil spring 103e, as shown in FIG. 5A. In addition, in FIG. 5A, the movable portion 103c is formed into a right-angled triangular column.

In the configuration shown in FIGS. 5A to 5C, when the surgical instrument 100 is mounted on the arm portion 200, the columnar portion 103b of the surgical instrument 100 receives a pressing force in the B1 direction shown in FIG. 5B due to the columnar portion 201. Due to the pressing force in the B1 direction, the movable portion 103c abuts on the tooth of the gear 101 while being at a right angle to the columnar portion 103b, and a torque in the A direction shown in FIG. 5B is applied to the gear 101. Consequently, the gear 101 rotates by a predetermined angle in accordance with the torque in the A direction applied by the movable portion 103c.

When the surgical instrument 100 is detached from the arm portion 200, the columnar portion 103b receives a pressing force in the B2 direction shown in FIG. 5C due to the restoring force of the coil spring 103a. Due to this pressing force in the B2 direction, the columnar portion 103b moves in the B2 direction. At this time, the movable portion 103c moves by receiving a pressing force in the C2 direction shown in FIG. 5C from the tooth of the gear 101. However, since the movable portion 103c is formed into a right-angled triangular column, the torque in the A direction shown in FIG. 5B is not applied to the gear 101. Consequently, the gear 101 does not reversely rotate. Thereafter, the movable portion 103c moves in the C1 direction shown in FIG. 5B due to the restoring force of the coil spring 103e, whereby the movable portion 103c is engaged again with the gear 101.

Even in the configuration of FIGS. 5A to 5C described above, it is possible to configure the gear-moving mechanism that rotates the gear 101 in the A direction by a predetermined angle only when the surgical instrument 100 is mounted on the arm portion 200.

FIGS. 5A to 5C shows a configuration in which by forming the lower surface of the movable portion 103c into a slope, the gear 101 is configured to rotate when the columnar portion 103b moves in the B1 direction, that is, when the surgical instrument 100 is mounted on the arm portion 200. A configuration may also be made in which by forming the upper surface of the movable portion 103c into a slope contrary to the above configuration, the gear 101 is configured to rotate when the columnar portion 103b moves in the B2 direction, that is, when the surgical instrument 100 is detached from the arm portion 200.

In the examples of FIGS. 1A to 5C described above, the rotation number of the gear 101 is measured by the potentiometer 102. However, the potentiometer 102 is not necessarily used.

Figure 6:
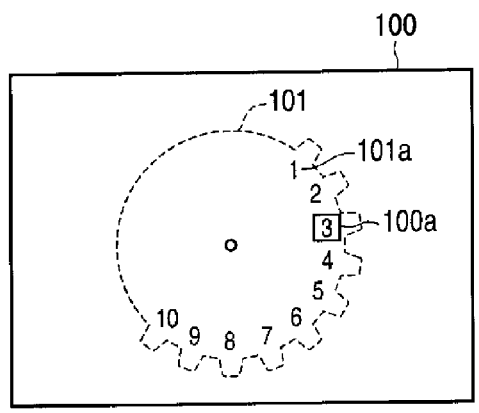
FIG. 6 is a view showing a modified example in which the usage count of the surgical instrument can be visually confirmed.

For example, as shown in FIG. 6, a window 100a may be provided at the body of the surgical instrument 100, and a number 101a may be formed (by printing, engraving, or the like) at the position on the gear 101, which is a position corresponding to each rotation angle of the gear per one rotation. In this configuration, the number 101a shown from the window 100a changes whenever the gear 101 rotates once. In this manner, the usage count of the surgical instrument 100 can be visually checked. With this configuration, it is not necessary to provide the potentiometer 102. In this case, there is no electric contact between the surgical instrument 100 and the arm portion 200, and accordingly, a configuration that is more resistant to sterilization or the like is obtained.

It is also possible to provide the potentiometer 102 simultaneously. In this case, when the surgical instrument 100 is detached from the arm portion 200, the remaining usage count can be confirmed by visual checking.

Figure 7:
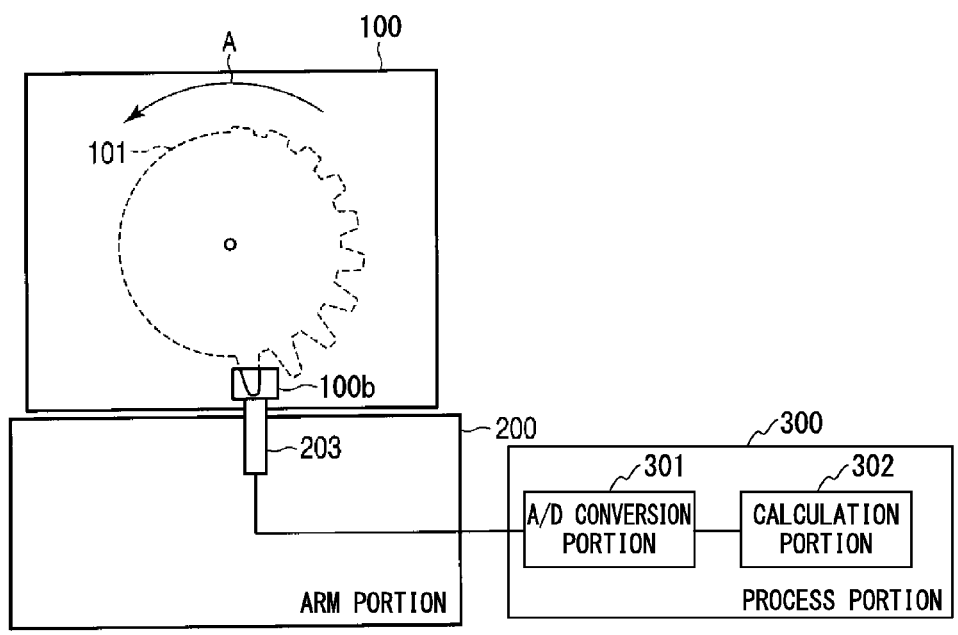
FIG. 7 is a view showing a modified example in which the usage count of the surgical instrument is measured by a capacity sensor.

The rotation number of the gear 101 may also be measured in a non-contact manner. FIG. 7 is an example of measuring the rotation number of the gear 101 by using a capacity sensor. In the example shown in FIG. 7, the gear 101 is configured with a metallic material, and each tooth formed in the gear 101 is formed such that each tooth has a different height from the center of the gear 101. In addition, a capacity sensor 203 is provided at the arm portion 200.

Since the heights of the teeth formed in the gear 101 are different from each other, the distance between the tooth of the gear 101 and the capacity sensor 203 changes with the rotation number of the gear 101. As a result, capacitance between the tooth of the gear 101 and the capacity sensor 203 changes. The change in capacitance can be detected as the rotation number of the gear 101, that is, as the usage count of the surgical instrument 100. In addition, if the window 100b is provided at the surgical instrument 100, it is possible to visually check the height of the tooth formed in the gear 101. Consequently, it is also possible to check the rotation number of the gear 101.

Figure 8A:
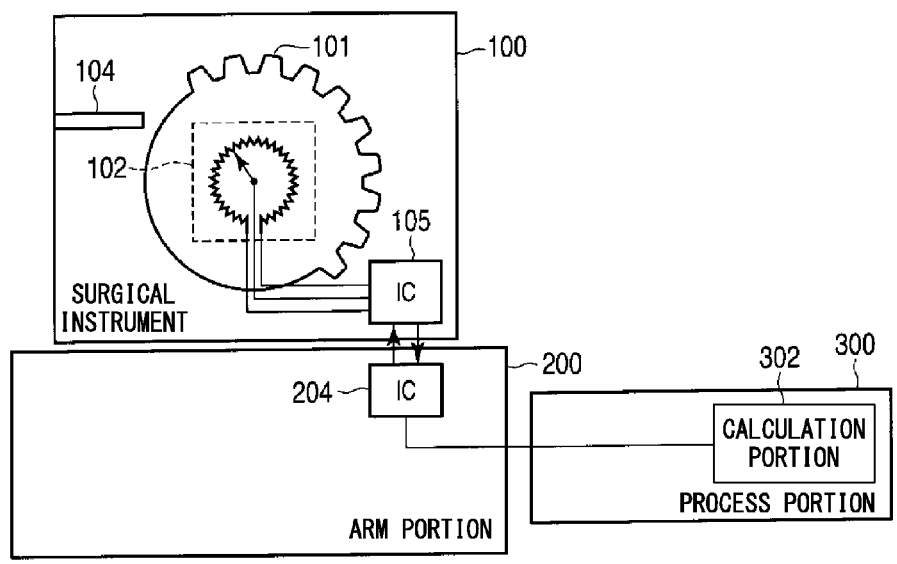
FIG. 8A is a view showing a modified example in which the usage count of the surgical instrument is wirelessly communicated to the arm portion.
Figure 8B:
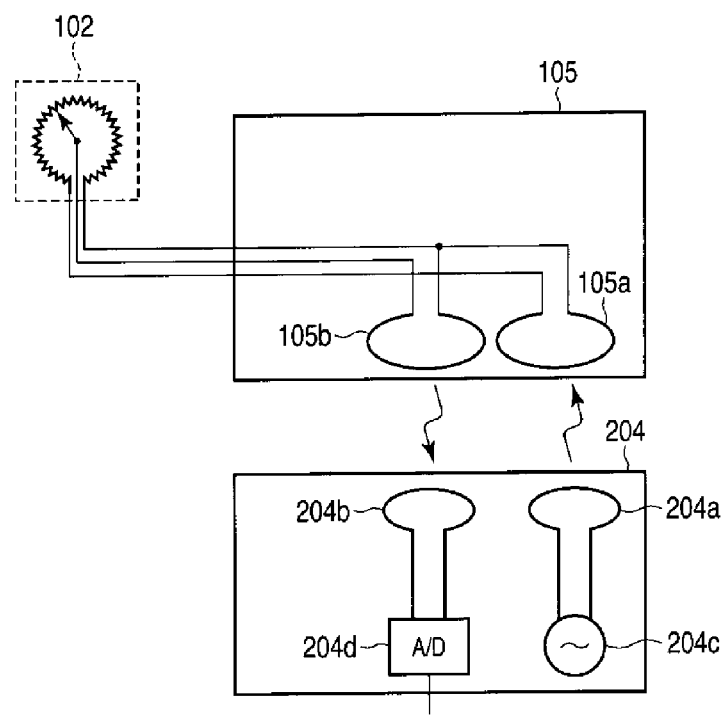
FIG. 8B is a view showing the modified example in which the usage count of the surgical instrument is wirelessly communicated to the arm portion.

As shown in FIG. 8A, an IC for wireless communication as a wireless communication portion may be provided at both the surgical instrument 100 and the arm portion 200. Consequently, the measurement results of the potentiometer 102 can be wirelessly communicated. FIG. 8B shows a configuration example of an IC (a wireless communication portion) 105 for wireless communication of the surgical instrument 100 and an IC (a wireless communication portion) 204 for wireless communication of the arm portion 200.

The IC 105 for wireless communication has loop antennas 105a and 105b. The loop antenna 105a is connected to both ends of the resistive element portion of the potentiometer 102. In addition, the loop antenna 105a supplies power transmitted by inductive coupling between a loop antenna 204a of the IC 204 for wireless communication and the loop antenna 105a to the potentiometer 102. One end of the loop antenna 105b is connected to the rotating contact portion of the potentiometer 102, and the other end thereof is connected to one end (ground side) of the potentiometer 102. By inductive coupling between a loop antenna 204b of the IC 204 for wireless communication and the loop antenna 105b, the loop antenna 105b transmits the voltage value V corresponding to the resistance value of the potentiometer 102 to the loop antenna 204b of the IC 204 for wireless communication.

The IC 204 for wireless communication has the loop antennas 204a and 204b, a power supply 204c, and an A/D conversion portion 204d. The loop antenna 204a is connected to the power supply 204c. In addition, by inductive coupling between the loop antenna 204a and the loop antenna 105a of the IC 105 for wireless communication, the loop antenna 204a supplies power generated in the power supply 204c to the potentiometer 102. The loop antenna 204b is connected to the A/D conversion portion 204d. In addition, the loop antenna 204b outputs the voltage value V transmitted by inductive coupling between the loop antenna 204b and the loop antenna 105b of the IC 105 for wireless communication to the A/D conversion portion 204d.

The power supply 204c is a power supply for supplying power to the potentiometer 102. The A/D conversion portion 204d converts the voltage value V transmitted through the loop antenna 204b into a digital value.

Even in the configuration shown in FIGS. 8A and 8B, electric contact is not necessary between the surgical instrument 100 and the arm portion 200. Accordingly, a configuration that is more resistant to sterilization or the like is obtained.

Second Embodiment

Figure 9:
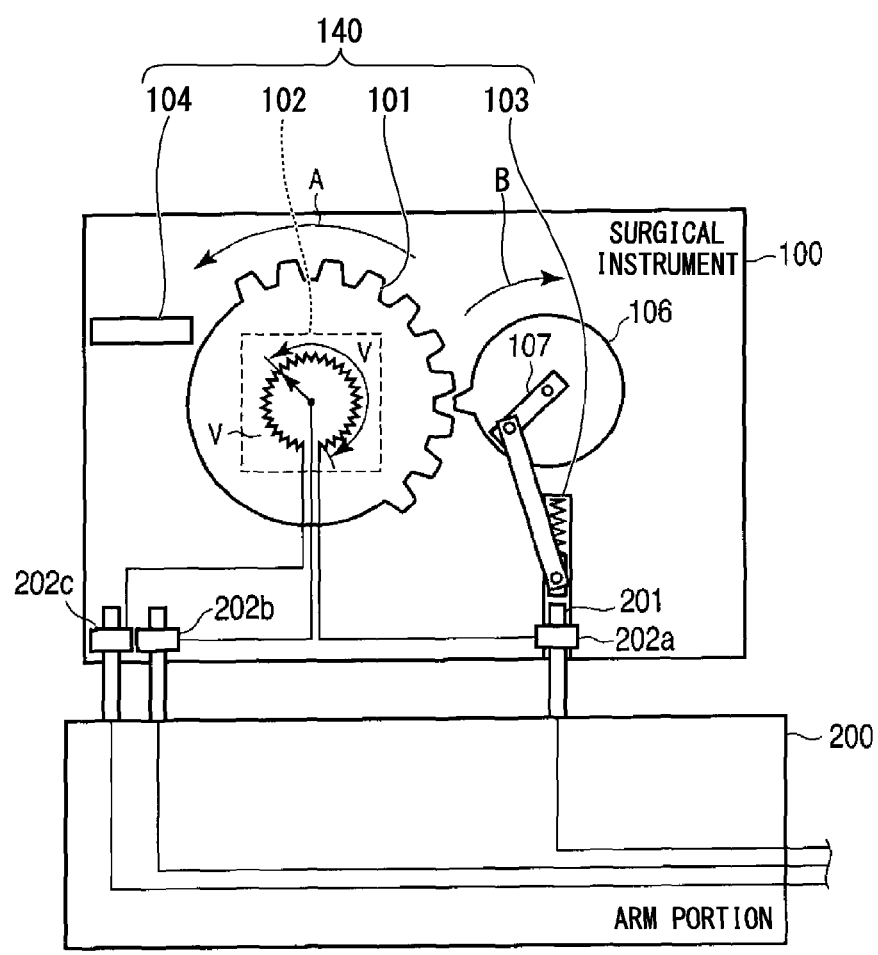
FIG. 9 is a view showing a configuration of a surgical operation support system according to a second embodiment of the present invention.

Next, a second embodiment of the present invention is described. FIG. 9 is a view showing a configuration of a surgical operation support system according to the second embodiment of the present invention. Herein, FIG. 9 illustrates particularly the configuration of the usage count accumulation portion according to the second embodiment.

The surgical instrument 100 according to the second embodiment includes the usage count accumulation portion 140. In FIG. 9, the usage count accumulation portion 140 includes the gear 101 (first gear), the potentiometer 102, the gear-moving mechanism 103, and the rotation preventing member 104. In addition, the gear-moving mechanism 103 according to the second embodiment includes a gear 106 (second gear) and a link mechanism 107.

The rotation axis of the gear 106 is attached to the link mechanism 107. In the gear 106, one tooth is formed so as to be engaged with the gear 101. The link mechanism 107 is configured to convert the pressing force from the columnar portion 201 of the arm portion 200 into a torque of the gear 106.

In the configuration shown in FIG. 9, when the surgical instrument 100 is mounted on the arm portion 200, a coil spring that is provided at the link mechanism 107 receives a pressing force in the vertical direction due to the columnar portion 201 of the arm portion 200. Due to this pressing force, the link mechanism 107 operates, and the gear 106 is engaged with the gear 101 while rotating in the B direction shown in FIG. 9. As a result, a torque in the A direction is applied to the gear 101, whereby the gear 101 rotates by a predetermined angle.

When the surgical instrument 100 is detached from the arm portion 200, due to the restoring force of the coil spring provided at the link mechanism 107, the gear 101 is disengaged from the gear 106.

As described above, in the present embodiment, the usage count of the surgical instrument 100 can also be mechanically measured. Accordingly, it is possible to configure a surgical instrument that is resistant to sterilization treatment or the like and excellent in durability.

FIG. 9 shows an example of measuring the rotation number of the gear 101 by the potentiometer 102. Even in FIG. 9, the rotation number of the gear 101 is not necessarily measured by the potentiometer 102. In FIG. 9, it is also possible to apply various modified examples shown in the first embodiment.

Third Embodiment

Figure 10A:
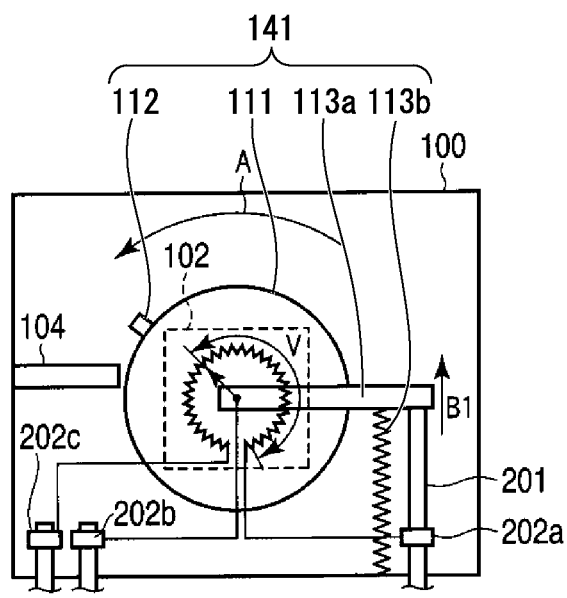
FIG. 10A is a view showing a configuration of a surgical operation support system according to a third embodiment of the present invention.
Figure 10B:
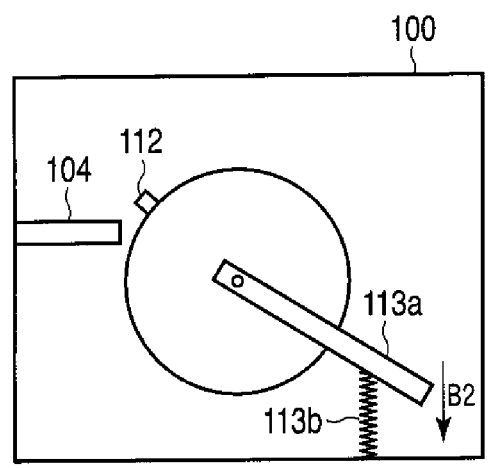
FIG. 10B is a view showing the configuration of the surgical operation support system according to the third embodiment of the present invention.

Next, a third embodiment of the present invention is described. FIGS. 10A and 10B are views showing a configuration of a surgical operation support system according to the third embodiment of the present invention. Herein, FIGS. 10A and 10B illustrate particularly the configuration of the usage count accumulation portion according to the third embodiment.

As shown in FIG. 10A, the surgical instrument 100 according to the third embodiment includes, as a usage count accumulation portion, a ratchet type rotation mechanism (a usage count accumulation portion) 141. The ratchet type rotation mechanism 141 includes a rotation portion (a moving portion) 111 and a projection portion (a moving portion) 112, a link (a moving mechanism) 113a, and a coil spring (a moving mechanism) 113b.

In the rotation portion 111, the potentiometer 102 is formed. In addition, the surgical instrument 100 according to the present embodiment is configured to change the resistance value (the voltage value) measured in the potentiometer 102 by the rotation of the rotation portion 111. Near the rotation axis of the rotation portion 111, a ratchet mechanism which is configured to rotate the body of the rotation portion 111 only in the A direction shown in FIG. 10A is provided. Moreover, in the rotation portion 111, the projection portion 112 is formed. The projection portion 112 is provided such that the projection portion 112 abuts on the rotation preventing member 104 after the rotation portion 111 rotates a predetermined number of times so as to restrict the rotation portion 111 from rotating any more.

The link 113a is attached to a portion of the rotation axis of the rotation portion 111. The link 113a is pushed up in the B1 direction by being pressed by the columnar portion 201 of the arm portion 200, thereby applying a torque for rotating the rotation portion 111 to the rotation portion 111.

In the configuration shown in FIGS. 10A and 10B, when the surgical instrument 100 is mounted on the arm portion 200, the link 113a is pushed up by the columnar portion 201 of the arm portion 200 as shown in FIG. 10A, whereby a torque in the A direction shown in FIG. 10A is applied to the rotation portion 111. As a result, the rotation portion 111 rotates in the A direction by a predetermined angle.

When the surgical instrument 100 is detached from the arm portion 200, due to the restoring force of the coil spring 113b, the link 113a is pushed down in the B2 direction as shown in FIG. 10B, whereby a torque in a direction opposite to the A direction shown in FIG. 10A is applied to the rotation portion 111. However, due to the action of the ratchet mechanism, the rotation of the rotation portion 111 is restricted, whereby the rotation portion 111 does not rotate in a direction opposite to the A direction shown in FIG. 10A.

As described above, in the present embodiment, the usage count of the surgical instrument 100 can also be mechanically measured. Accordingly, it is possible to configure a surgical instrument that is resistant to sterilization treatment or the like and excellent in durability.

FIGS. 10A and 10B show an example of measuring the rotation number of the rotation portion 111 by the potentiometer 102. Even in FIGS. 10A and 10B, the rotation number of the rotation portion 111 is not necessarily measured by the potentiometer 102. In FIGS. 10A and 10B, it is also possible to apply various modified examples shown in the first embodiment.

Fourth Embodiment

Figure 11:
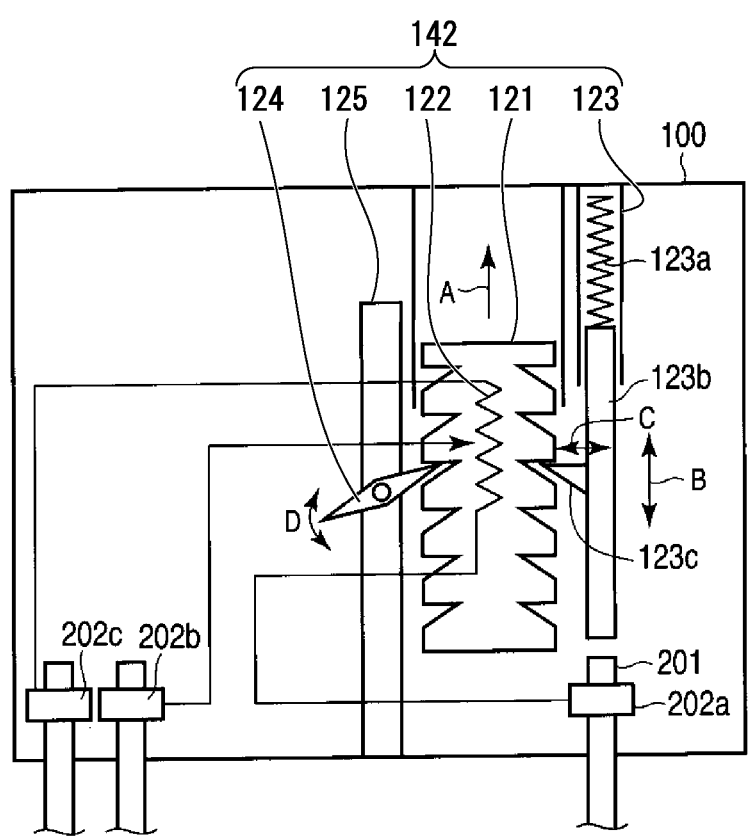
FIG. 11 is a view showing a configuration of a surgical operation support system according to a fourth embodiment of the present invention.

Next, a fourth embodiment of the present invention is described. FIG. 11 is a view showing a configuration of a surgical operation support system of the fourth embodiment of the present invention. Herein, FIG. 11 illustrates particularly the configuration of a usage count accumulation portion according to the fourth embodiment.

The surgical instrument 100 according to the fourth embodiment includes a ratchet type linear driving mechanism (a usage count accumulation portion) 142 as a usage count accumulation portion as shown in FIG. 11. The ratchet type linear driving mechanism 142 includes a linear driving movement portion 121, a linear driving potentiometer 122, a linear driving movement mechanism 123, a restriction member 124, and a columnar portion 125. In addition, the linear driving mechanism 123 includes a coil spring 123a, a columnar portion 123b, and a movable portion 123c.

In the linear driving movement portion 121, concave portions formed in the shape of right-angled triangular prism are formed at a constant interval. In addition, the linear driving movement portion 121 is configured to freely move in the A direction shown in FIG. 11 by a predetermined amount. The linear driving potentiometer 122 is formed on the linear driving movement portion 121, and is configured to change the resistance value in accordance with the linear driving movement of the linear driving movement portion 121 in the A direction.

The linear driving movement mechanism 123 has the same configuration as that of the gear-moving mechanism according to the first embodiment, which is shown in FIGS. 5A to 5C as an example. The detailed operation thereof is described later.

The restriction member 124 is an approximately rhombic member that is supported on the columnar portion 125 so as to be able to rotate in the D direction shown in FIG. 11 and to be approximately orthogonal to the linear driving movement portion 121. The restriction member 124 is formed so as to fit in the concave portion formed in the linear driving movement portion 121, and restricts the linear driving movement mechanism 123 to move only in the A direction shown in FIG. 11. The columnar portion 125 is fixed to the body of the surgical instrument 100 so as to support the restriction member 124.

In the configuration shown in FIG. 11, when the surgical instrument 100 is mounted on the arm portion 200, the columnar portion 123b of the surgical instrument 100 receives a pressing force in the B direction (upward direction in the drawing) shown in FIG. 11. Due to this pressing force in the upward direction, the movable portion 123c fits into the concave portion formed in the linear driving movement portion 121 while being at a right angle to the columnar portion 123b. At this time, the pressing force in the A direction shown in FIG. 11 is applied to the linear driving movement portion 121. At this time, the state where the restriction member 124 fits in the linear driving movement portion 121 is temporarily released. Due to such operations, the linear driving movement portion 121 linearly moves a predetermined distance in accordance with the pressing force in the A direction applied by the movable portion 123c. At this time, the movable portion 123c fits into the concave portion formed in the linear driving movement portion 121. At this time, the restriction member 124 also fits into the concave portion formed in the linear driving movement portion 121.

When the surgical instrument 100 is detached from the arm portion 200, the columnar portion 123b receives a pressing force in the B direction (downward direction in the drawing) due to the restoring force of the coil spring 123a. Due to the pressing force in the downward direction, the columnar portion 123b moves one step downward. At this time, the movable portion 123c receives a pressing force in the C direction (right direction in the drawing) shown in FIG. 11 from the linear driving movement portion 121, and consequently, the state where the movable portion 123c fits in the linear driving portion 121 is temporarily released. However, the state where the restriction member 124 fits in the linear driving movement portion 121 is not released, and the movement of the linear driving movement portion 121 in a direction opposite to the A direction is restricted. As a result, the position of the restriction portion 121 is held. Subsequently, due to the restoring force of a coil spring (not shown) provided between the columnar portion 123b and the movable portion 123c, the movable portion 123c moves in the C direction (left direction in the drawing). In addition, the movable portion 123c fits into the concave portion formed in the linear driving movement portion 121.

As described above, in the present embodiment, the usage count of the surgical instrument 100 can also be mechanically measured. Accordingly, it is possible to configure a surgical instrument that is resistant to sterilization treatment or the like and excellent in durability.

In FIG. 11, the measurement results of the potentiometer 102 may be wirelessly communicated, or numbers may be formed in the linear driving movement portion 121.

Fifth Embodiment

Figure 12A:
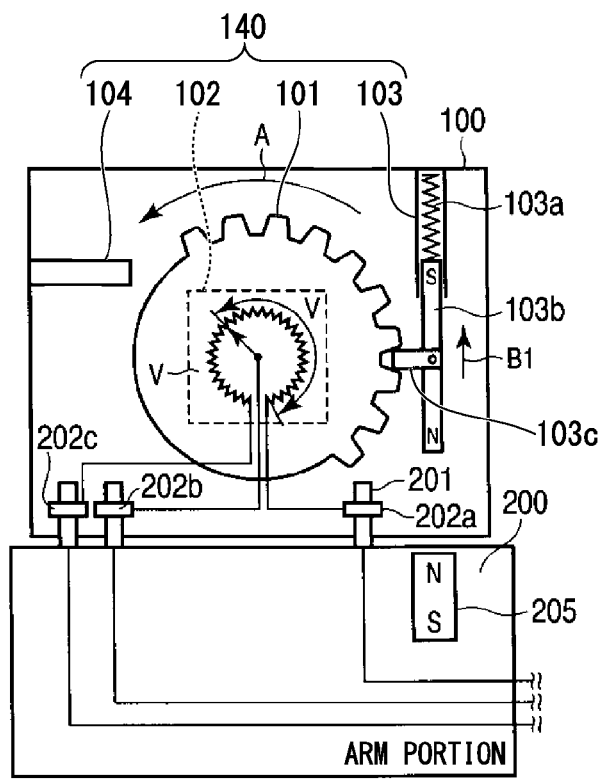
FIG. 12A is a view showing a configuration of a surgical operation support system according to a fifth embodiment of the present invention.
Figure 12B:
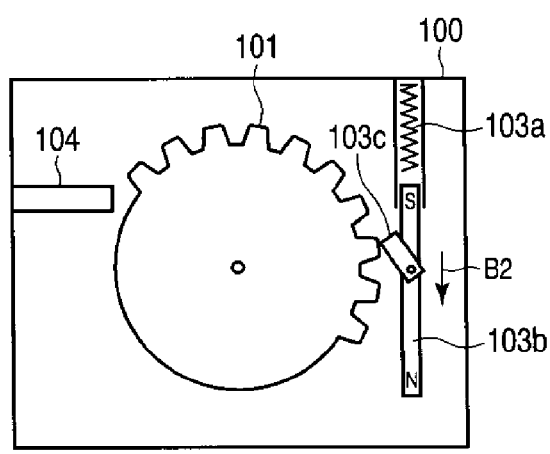
FIG. 12B is a view showing the configuration of the surgical operation support system according to the fifth embodiment of the present invention.

Next, a fifth embodiment of the present invention is described. FIGS. 12A and 12B are views showing a configuration of a surgical operation support system according to the fifth embodiment of the present invention. Herein, FIGS. 12A and 12B illustrate particularly the configuration of the usage count accumulation portion according to the fifth embodiment.

The configuration of the surgical instrument 100 according to the fifth embodiment is almost the same as the configuration of the surgical instrument according to the first embodiment, which is shown in FIG. 2 as an example. The surgical instrument 100 according to the fifth embodiment is different in that the columnar portion 103b is composed of a magnet. In addition, in the fifth embodiment, a magnet 205 is provided at the arm portion 200. The magnet 205 is disposed such that a side of the columnar portion 103b and a side of the magnet 205, which are sides facing each other, exhibit the same polarity.

In the configuration shown in FIGS. 12A and 12B, when the surgical instrument 100 is mounted on the arm portion 200, the columnar portion 103b of the surgical instrument 100 receives a pressing force in the B1 direction shown in FIG. 12A by the magnet 205, in a non-contact manner. Due to the pressing force in the B1 direction, the movable portion 103c abuts on the tooth of the gear 101 while maintaining a right angle to the columnar portion 103b, whereby a torque in the A direction shown in FIG. 12A is applied to the gear 101. As a result, the gear 101 rotates by a predetermined angle in accordance with the torque in the A direction applied by the movable portion 103c.

When the surgical instrument 100 is detached from the arm portion 200, due to the restoring force of the coil spring 103a, the columnar portion 103b receives a pressing force in the B2 direction shown in FIG. 12B. Due to the pressing force in the B2 direction, the columnar portion 103b moves in the B2 direction. At this time, the movable portion 103c abuts on the tooth of the gear 101. However, due to the action of the helical spring 103d, a torque in the A direction shown in FIG. 12A is not applied to the gear 101, and the movable portion 103c rotates, whereby the gear 101 is temporarily disengaged from the movable portion 103c. Consequently, the gear 101 does not rotates in a direction opposite to the A direction shown in FIG. 12A. Thereafter, due to the restoring force of the helical spring 103d, the movable portion 103c rotates in the C1 direction, whereby the movable portion 103c is engaged again with the gear 101.

As described above, in the present embodiment, the usage count of the surgical instrument 100 can also be mechanically measured. Accordingly, it is possible to configure a surgical instrument that is resistant to sterilization treatment or the like and excellent in durability. In addition, in the fifth embodiment, it is not necessary to provide the surgical instrument 100 with the portion for inserting the columnar portion 201. Therefore, it is possible to configure a surgical instrument that is more resistant to sterilization treatment and excellent in durability, compared to the first embodiment.

In the present embodiment, the magnet 205 is disposed such that a side of the columnar portion 103b and a side of the magnet 205, which are sides facing each other, exhibit the same polarity, whereby the usage count of the surgical instrument 100 is measured. Contrary to this, the magnet 205 may be disposed such that a side of the columnar portion 103b and a side of the magnet 205, which are sides facing each other, exhibit the opposite polarity, whereby the usage count of the surgical instrument 100 may be measured. In this case, when the surgical instrument 100 is mounted on the arm portion 200, due to the magnetic force between the columnar portion 103b and the magnet 205, the columnar portion 103b of the surgical instrument 100 moves in the B2 direction shown in FIG. 12B. In addition, the gear 101 rotates in a direction opposite to the A direction, whereby the usage count of the surgical instrument 100 is measured. Accordingly, the direction of the biasing force of the coil spring 103a or the rotation state of the movable portion 103c becomes opposite to that of the present embodiment.

FIGS. 12A and 12B show an example of measuring the rotation number of the gear 101 by the potentiometer 102. Even in FIGS. 12A and 12B, the rotation number of the gear 101 is not necessarily measured by the potentiometer 102. In FIGS. 12A and 12B, it is also possible to apply various modified examples shown in the first embodiment.

While preferred embodiments of the present invention have been described, the present invention is not limited to the embodiments. Additions, omissions, substitutions, and other modifications can be made to the present invention without departing from the spirit and scope of the present invention. The present invention is not limited to the above-mentioned description, and is only limited by the scope of the appended claims.

What is claimed is:

1. A surgical operation support system comprising:
an arm;
a surgical instrument configured to be removably attached to the arm, wherein the surgical instrument comprises a first gear, a second gear, and a link, wherein, in response to an attachment of the surgical instrument to the arm or a detachment of the surgical instrument from the arm:
the link is configured to receive a force to drive the link,
the link is operatively connected to the second gear such that the link is configured to convert the force into a rotation of the second gear; and
the second gear is operatively connected to the first gear such that the rotation of the second gear engages the second gear to the first gear to cause a rotation of the first gear; and
a sensor configured to sense the rotation of the first gear as an indicator of a usage count of the surgical instrument.

2. The surgical operation support system according to claim 1,
wherein the arm comprises a magnet, and
wherein in response to the attachment of the surgical instrument to the arm or the detachment of the surgical instrument from the arm, the link is configured to receive a magnetic force, in a non-contact manner, from the magnet of the arm as the force to drive the link.

3. The surgical operation support system according to claim 1,
wherein the first gear comprises a plurality of teeth, wherein each tooth of the first gear has a different height from a center of the first gear, and
wherein the sensor is configured to sense the height of a tooth of the plurality of teeth of the first gear as the indicator of the usage count of the surgical instrument.

4. A surgical operation support system comprising:
an arm; and
a surgical instrument configured to be removably attached to the arm, wherein the surgical instrument comprises:
a gear;
a link configured to, in response to the surgical instrument being attached to the arm or the surgical instrument being detached from the arm, receive a force to drive the link, and convert the force to rotate the gear by a predetermined amount;
a potentiometer configured to accumulate a usage count of the surgical instrument by changing a resistance value according to the predetermined amount by which the gear rotated; and
a circuit configured to output a voltage value based on the resistance value that is changed by the potentiometer.

5. The surgical operation support system according to claim 4,
wherein the circuit configured to output the voltage value based on the resistance value that is changed by the potentiometer, comprises electrodes that are connected to the potentiometer, and
wherein the electrodes are configured to output the voltage value by being electrically connected to the link when the surgical instrument is attached to the arm.

6. The surgical operation support system according to claim 4,
wherein the circuit configured to output the voltage value based on the resistance value that is changed by the potentiometer, comprises a wireless communication circuit configured to wirelessly communicate the voltage value.

7. A surgical instrument comprising:
a first gear;
a second gear;
a link, wherein, in response to an attachment of the surgical instrument to an arm or a detachment of the surgical instrument from the arm:
the link is configured to receive a force to drive the link;
the link is operatively connected to the second gear such that the link is configured to convert the force into a rotation of the second gear; and
the second gear is operatively connected to the first gear such that the rotation of the second gear engages the second gear to the first gear to cause a rotation of the first gear; and
a sensor configured to sense the rotation of the first gear as an indicator of a usage count of the surgical instrument.

8. The surgical instrument according to claim 7,
wherein the first gear comprises a plurality of teeth, wherein each tooth of the first gear has a different height from a center of the first gear, and wherein the sensor is configured to sense the height of a tooth of the plurality of teeth of the first gear as the indicator of the usage count of the surgical instrument.

9. A surgical instrument comprising:
a gear;
a link configured to, in response to the surgical instrument being attached to an arm or the surgical instrument being detached from the arm, receive a force to drive the link, and convert the force to rotate the gear by a predetermined amount;
a potentiometer configured to accumulate a usage count of the surgical instrument by changing a resistance value according to the predetermined amount by which the gear rotated; and
a circuit configured to output a voltage value based on the resistance value that is changed by the potentiometer.

10. The surgical instrument according to claim 9,
wherein the circuit configured to output the voltage value based on the resistance value that is changed by the potentiometer, comprises electrodes that are connected to the potentiometer, and
wherein the electrodes are configured to output the voltage value by being electrically connected to the link when the surgical instrument is attached to the arm.

11. The surgical instrument according to claim 9,
wherein the circuit configured to output the voltage value based on the resistance value that is changed by the potentiometer, comprises a wireless communication circuit configured to wirelessly communicate the voltage value.

* * * * *